US010864191B2

(12) United States Patent
Odergren

(10) Patent No.: US 10,864,191 B2
(45) Date of Patent: Dec. 15, 2020

(54) 5-HT6 RECEPTOR ANTAGONISTS FOR USE IN THE TREATMENT OF ALZHEIMER'S DISEASE WITH APATHY AS COMORBIDITY

(71) Applicant: H. Lundbeck A/S, Valby (DK)

(72) Inventor: Karl Tomas Odergren, Stockholm (SE)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 15/587,935

(22) Filed: May 5, 2017

(65) Prior Publication Data

US 2017/0326107 A1    Nov. 16, 2017

(30) Foreign Application Priority Data

May 11, 2016   (DK) ................................ 2016 00286

(51) Int. Cl.
| | | |
|---|---|---|
| *A61K 31/4045* | (2006.01) | |
| *A61K 31/519* | (2006.01) | |
| *A61K 45/06* | (2006.01) | |
| *A61K 31/496* | (2006.01) | |
| *A61K 31/27* | (2006.01) | |
| *A61K 31/325* | (2006.01) | |
| *A61K 31/445* | (2006.01) | |
| *A61K 31/55* | (2006.01) | |

(52) U.S. Cl.
CPC .......... *A61K 31/4045* (2013.01); *A61K 31/27* (2013.01); *A61K 31/325* (2013.01); *A61K 31/445* (2013.01); *A61K 31/496* (2013.01); *A61K 31/519* (2013.01); *A61K 31/55* (2013.01); *A61K 45/06* (2013.01)

(58) Field of Classification Search
CPC ................................................. A61K 31/4045
See application file for complete search history.

(56) References Cited

U.S. PATENT DOCUMENTS

| | | |
|---|---|---|
| 8,309,559 B2 | 11/2012 | Savchuk et al. |
| 8,471,009 B2 | 6/2013 | Ivashchenko et al. |
| 8,552,005 B2 | 10/2013 | Ivashchenko et al. |
| 8,629,154 B2 | 1/2014 | Ivashchenko et al. |
| 8,829,009 B2 | 9/2014 | Ivashchenko et al. |
| 2015/0320742 A1 | 11/2015 | Chuang et al. |

FOREIGN PATENT DOCUMENTS

| | | |
|---|---|---|
| EP | 2037925 | 3/2009 |
| WO | WO 2002/078693 | 10/2002 |
| WO | WO 2008/002539 | 1/2008 |
| WO | WO 2008002539 A1 * | 1/2008 |
| WO | WO 2009/093206 | 9/2009 |
| WO | WO 2014/037532 | 3/2014 |
| WO | WO 2014037532 A1 * | 3/2014 |

OTHER PUBLICATIONS

Wilkinson et al, Lancet Neurol. 13:1092-1099, 2014.*
NCT02006641, available online on Dec. 10, 2015 at https://clinicaltrials.gov/ct2/history/NCT02006641?V_9=View#StudyPageTop.*
Starkstein et al., Syndromic Validity of Apathy in Alzheimer's Disease, Am J Psychiatry 2001; 158:872-877.*
Aricept® (donepezil hydrochloride) drug label, Revised: Feb. 2021.*
Exelon® patch (rivastigmine transdermal system), Approved: Apr. 21, 2000.*
Razadyne® ER (galantamine hydrobromide) drug lable, Approved: 2001.*
Wilkinson et al, The Journal of the Alzheimer Association, vol. 9, Issue 4, P529 (2013).*
PubChem CID: 11256720, CAS Registry No. 607742-69-8 (Created: Oct. 26, 2006).
Arnt, J. et al. (2010) "Lu AE58054, a 5-HT$_6$Receptor Antagonist, Reverses Cognitive Impairment Induced by Subchronic Phencyclidine in a Novel Object Recognition Test in Rats," Int. J. Neuropsychopharmacol. 13:1021-1033.
Berge, S.M. et al. (1977) "Pharmaceutical Salts," J. Pharm. Sci. 66:1-19.
Cummings, J.L. et al. (1994) "The Neuropsychiatric Inventory: Comprehensive Assessment of Psychopathology in Dementia," Neurology 44(12):2308-2314.
Galasko, D. et al. (1997) "An Inventory to Assess Activities of Daily Living for Clinical Trials in Alzheimer's Disease," Alzheimer Dis. Assoc. Disord. 11(Suppl 2): S22-S32.
Olanow, C.W. et al. (2014) "Continuous Intrajejunal Infusion of Levodopa-Carbidopa Intestinal Gel for Patients With Advanced Parkinson's Disease: A Randomised, Controlled, Double-Blind, Double-Dummy Study," Lancet Neurol. 3(2):141-149.
Rosen, W.G. et al. (1984) "A New Scale for Alzheimer's Disease," Am. J. Psychiatry 141:1356-1364.
Herrick, K.F., et al. (2016) "The 5-HT$_6$ Receptor Antagonist Idalopirdine Potentiates the Effects of Acetylcholinesterase Inhibition on Neuronal Network Oscillations and Extracellular Acetylcholine Levels in the Rat Dorsal Hippocampus," Neuropharmacol. 107:351-363.
International Search Report PCT/EP2017/060979 (2017) (5 pages).
Johnson, C.N., et al. (2008) "5-HT$_6$ Receptor Antagonists: Prospects for the Treatment of Cognitive Disorders Including Dementia," Current Opin. Drug Disc. & Develop. 11(5):642-654.
Starkstein, S.E., et al. (2006) "A Prospective Longitudinal Study of Apathy in Alzheimer's Disease," J. Neurol. Neurosurg. Psychiatry 77:8-11.
Wilkinson, D., et al. (2014) "Safety and Efficacy of Idalopirdine, a 5-HT$_6$ Receptor Antagonist, in Patients with Moderate Alzheimer's Disease (LADDER): a Randomised, Double-Blind, Placebo-Controlled Phase 2 Trial," Lancet Neurol, 13:1092-1099.
Written Opinion of the International Searching Authority PCT/EP2017/060979 (2017) (8 pages).

(Continued)

*Primary Examiner* — Svetlana M Ivanova
(74) *Attorney, Agent, or Firm* — Wilmer Cutler Pickering Hale and Dorr LLP

(57) ABSTRACT

The present invention relates to 5-HT$_6$ receptor antagonists for the treatment of Alzheimer's disease with comorbid apathy comprising administering an effective dose of a 5-HT$_6$ receptor antagonist to improve or augment the effect of an acetylcholinesterase inhibitor.

15 Claims, No Drawings

(56) References Cited

OTHER PUBLICATIONS

Wilkinson et al., "A Clinical Phase II Study of Lu AE58054 Added to Stable Donepezil Treatment in Patients with Moderate Alzheimer's Disease," Alzheimer's & Dementia: The Journal of the Alzheimer's Association, vol. 9, Issue 4, P529 (2013).
U.S. Department of Health & Human Services and U.S. Food & Drug Administration, "Paving the Way for Personalized Medicine—FDA's Role in a New Era of Medical Product Development," 62 total pages: cover page and pp. 1-61 (Oct. 2013).
Galimberti, D. and Scarpini, E., "Idalopirdine as a treatment for Alzheimer's disease," Expert Opin. Investig. Drugs [Early Online], vol. 24, No. 7, pp. 1-7 (2015).
Hampel, H., et al., "The Alzheimer Precision Medicine Initiative," J. Alzheimer's Disease, vol. 68, pp. 1-24 (2019).
Padala, P.R., et al., "Methylphenidate for Apathy in Community-Dwelling Older Veterans with Mild Alzheimer's Disease: A Double-Blind, Randomized, Placebo-Controlled Trial," Am. J. Psychiatry, vol. 175, No. 2, pp. 159-168 (Feb. 2018).
Rea, R., et al., "Apathy in Alzheimer's Disease: Any Effective Treatment?," The Scientific World Journal, Hindawi Publishing Corporation, Article ID 421385, pp. 1-9 (Feb. 2014).
Reitz, C., "Toward precision medicine in Alzheimer's disease," Ann. Transl. Med., vol. 4, No. 6: 107, pp. 1-7 (Jan. 2016).
Ruthirakuhan, M.T., et al., "Pharmacological interventions for apathy in Alzheimer's disease (Review)," Cochrane Database of Systematic Reviews, Issue 5, Art. No. CD012197, 101 total pages: cover, TOC, pp. 1-98 (2018).
Cummings, J.L. et al., (1994) "The Neuropsychiatric Inventory: Comprehensive Assessment of Psychopathology in Dementia," Neurology 44(12):2308-2314 (7 pages).
Cummings, Jeffrey L., (1997) "The Neuropsychiatric Inventory: Assessing Psychopathology in Dementia Patients," Neurology 48(Suppl. 6): S10-S16 (7 pages).
Liu et al., "Identification of a novel series of 3-piperidinyl-5-sulfonylindazoles as potent 5-HT6 ligands," Bioorganic & Medical Chemistry Letters, vol. 19, Issue 12, pp. 3214-3216. Available online May 3, 2009.

* cited by examiner

5-HT6 RECEPTOR ANTAGONISTS FOR USE IN THE TREATMENT OF ALZHEIMER'S DISEASE WITH APATHY AS COMORBIDITY

CROSS-REFERENCE TO RELATED APPLICATION

This application claims benefit of DK Patent Application No. PA 2016 00286, filed on May 11, 2016, which application is hereby incorporated by reference in its entirety.

FIELD OF THE INVENTION

The present invention relates to 5-$HT_6$ receptor antagonists for the treatment of Alzheimer's disease with comorbid apathy comprising administering a therapeutically effective amount of a 5-$HT_6$ receptor antagonist to improve or augment the effect of an acetylcholinesterase inhibitor.

BACKGROUND OF THE INVENTION

Dementia is a clinical syndrome characterized by deficits in multiple areas of cognition that cannot be explained by normal aging, a noticeable decline in function, and an absence of delirium. In addition, neuropsychiatric symptoms are often present already at first diagnosis and then increase in numbers and intensity over time as the disease progresses. The neuropsychiatric symptoms in Alzheimer's disease (AD) patients are diverse and range from apathy to agitation.

The use of selective 5-$HT_6$ receptor antagonists to treat cognitive dysfunction has been suggested and is based on several lines of reasoning. For example, selective 5-$HT_6$ receptor antagonists have been shown to modulate cholinergic and glutamatergic neuronal function. The activity of selective 5-$HT_6$ receptor antagonists has been demonstrated in animal models of cognitive function. Since the disclosure of the first selective 5-$HT_6$ receptor antagonists, there have been several reports on the activity of these selective compounds in in-vivo models of cognitive function.

N-(2-(6-fluoro-1H-indol-3-yl)ethyl)-3-(2,2,3,3-tetrafluoropropoxy)-benzylamine, INN-name idalopirdine, is a potent and selective 5-$HT_6$ receptor antagonist which is currently in clinical development. N-(2-(6-fluoro-1H-indol-3-yl)-ethyl)-3-(2,2,3,3-tetrafluoropropoxy)-benzylamine has also been disclosed as Lu AE58054.

N-(2-(6-fluoro-1H-indol-3-yl)ethyl)-3-(2,2,3,3-tetrafluoropropoxy)-benzylamine is for the first time disclosed in WO 02/078693 and a dose range for N-(2-(6-fluoro-1H-indol-3-yl)-ethyl)-3-(2,2,3,3-tetrafluoropropoxy)-benzylamine is disclosed in WO 2014/037532.

A randomised, double-blind, placebo-controlled phase 2 trial has been reported in *Lancet Neurol* 2014; 13:141-49 (published online Oct. 6, 2014). The study (hereinafter referred to as the LADDER study) assessed the effect on cognitive performance of idalopirdine in donepezil-treated patients with moderate AD.

Avineuro Pharmaceuticals is developing an oral small-molecule 5-$HT_6$ receptor antagonist, AVN-211 (CD-008-0173), for the potential treatment of the cognitive symptoms as well as for Alzheimer's disease. AVN-211 is a 3-sulfonyl-pyrazolo[1,5-a]pyrimidine derivative and is disclosed in WO 2009/093206 as 3-Benzenesulfonyl-5,7-dimethyl-2-methylsulfanyl-pyrazolo[1,5-a]pyrimidine.

Axovant Sciences Ltd is developing an oral small-molecule 5-$HT_6$ receptor antagonist, RVT-101 (SB-742457, CAS Registry Number 607742-69-8) for the potential treatment of Alzheimer's disease. RVT-101 is an 8-piperazin-1-yl quinoline derivative and is disclosed in WO 2009/093206 as 3-phenylsulfonyl-8-piperazin-1-yl-quinoline.

SUMMARY OF THE INVENTION

The present provides a treatment of Alzheimer's disease with a 5-$HT_6$ receptor antagonist as an adjunctive therapy to acetylcholinesterase inhibitors in subjects, e.g., patients, who exhibit comorbid apathy.

DETAILED DESCRIPTION OF THE INVENTION

Apathy is characterized by the loss of initiation and motivation to participate in activities, social withdrawal, and emotional indifference. Patients with apathy are at increased risk to progressively suffer from decreased daily function and specific cognitive deficits such as executive cognitive dysfunction. Therefore, such patients tend to more early rely on families to provide more care than other patients with Alzheimer's disease, which results in increased stress for families.

The inventors of the present invention have surprisingly found that apathy is a phenotypical marker for a subgroup of Alzheimer's disease patients with enhanced treatment response to the 5-$HT_6$ receptor antagonist idalopirdine in combination with the acetylcholinesterase inhibitor donepezil ((RS)-2-[(1-Benzyl-4-piperidyl)methyl]-5,6-dimethoxy-2,3-dihydroinden-1-one).

Since idalopirdine is a 5-$HT_6$ receptor antagonist with high specificity and virtually no binding to other pharmacological receptors it is believed that other 5-$HT_6$ receptor antagonists, such as AVN-211 and RVT-101, also will give rise to an enhanced treatment response in Alzheimer's disease patients with comorbid apathy.

Embodiments of the Invention

In the following embodiments of the invention are disclosed. The first embodiment is denoted E1, the second embodiment is denoted E2 and so forth.

E1 A 5-$HT_6$ receptor antagonist or a pharmaceutically acceptable salt thereof for use in treating Alzheimer's disease with comorbid apathy by improving or augmenting the effect of an acetylcholinesterase inhibitor.

E2 The embodiment of E1, wherein the 5-$HT_6$ receptor antagonist is selected from the group consisting of idalopirdine, AVN-211 and RVT-101 or pharmaceutically acceptable salts of said 5-$HT_6$ receptor antagonists.

E3 The embodiment of E1 or E2, wherein the 5-$HT_6$ receptor antagonist is idalopirdine or a pharmaceutically acceptable salt thereof.

E4 The embodiment of E1 or E3, wherein the 5-$HT_6$ receptor antagonist is the hydrochloride salt of idalopirdine.

E5 The embodiment of E1 or E2, wherein the 5-$HT_6$ receptor antagonist is AVN-211 or a pharmaceutically acceptable salt thereof.

E6 The embodiment of E1 or E2, wherein the 5-$HT_6$ receptor antagonist is RVT-101 or a pharmaceutically acceptable salt thereof.

E7 The embodiment of E1, wherein the acetylcholinesterase inhibitor is selected from the group consisting of donepezil, rivastigmine and galantamine or pharmaceutically acceptable salts of said acetylcholinesterase inhibitors.

E8 The embodiment of E1 or E7, wherein the acetylcholinesterase inhibitor is donepezil or a pharmaceutically acceptable salt thereof.

E9 The embodiment of E1 or E8, wherein the acetylcholinesterase inhibitor is the hydrochloride salt of donepezil.

E10 The embodiment of E1 or E7, wherein the acetylcholinesterase inhibitor is rivastigmine or a pharmaceutically acceptable salt thereof.

E11 The embodiment of E1 or E10, wherein the acetylcholinesterase inhibitor is the hydrochloride salt or the tartrate salt of rivastigmine.

E12 The embodiment of E1 or E7, wherein the acetylcholinesterase inhibitor is galantamine or a pharmaceutically acceptable salt thereof.

E13 The embodiment of E1 or E12, wherein the acetylcholinesterase inhibitor is the hydrobromide salt of galantamine.

E14 The embodiment of E1, E3 or E8, wherein the 5-$HT_6$ receptor antagonist is idalopirdine and the acetylcholinesterase inhibitor is donepezil.

E15 The embodiment of E1 or E14, wherein the 5-$HT_6$ receptor antagonist is the hydrochloride salt of idalopirdine and the acetylcholinesterase inhibitor is the hydrochloride salt of donepezil.

E16 The embodiment of E1, E14 or E15, wherein the dosage range of idalopirdine is from 10 mg/day to 90 mg/day.

E17 The embodiment of E1, E3, E4, E14 or E15, wherein the dosage range of idalopirdine is from 30 mg/day to 60 mg/day.

E18 The embodiment of E17, wherein the dosage of idalopirdine is 30 mg/day.

E19 The embodiment of E17, wherein the dosage of idalopirdine is 60 mg/day.

E20 The embodiment of E1, E8, E9, E14 or E15, wherein the dosage range of donepezil is from 2 mg/day to 25 mg/day, preferably from 5 mg/day to 23 mg/day.

E21 A pharmaceutical composition comprising:
(A) a 5-$HT_6$ receptor antagonist selected from the group consisting of one or more of: the compounds idalopirdine, RVT-101, AVN-211, and pharmaceutically acceptable salts of such compounds; and
(B) an acetylcholinesterase inhibitor selected from the group consisting of one or more of: the compounds donepezil, rivastigmine, galantamine, and pharmaceutically acceptable salts of such compounds;
for the treatment of Alzheimer's disease wherein apathy is comorbid with Alzheimer's disease.

E22 Use of a 5-$HT_6$ receptor antagonist selected from the group consisting of one or more of the compounds: idalopirdine, RVT-101, AVN-211, and pharmaceutically acceptable salts of such compounds, for the manufacture of a medicament for the treatment of Alzheimer's disease wherein apathy is comorbid with Alzheimer's disease.

E23 Use of:
(A) a 5-$HT_6$ receptor antagonist selected from the group consisting of one or more of: the compounds idalopirdine, RVT-101, AVN-211, and pharmaceutically acceptable salts of such compounds; and
(B) an acetylcholinesterase inhibitor selected from the group consisting of one or more of: the compounds donepezil, rivastigmine, galantamine, and pharmaceutically acceptable salts of such compounds;
for the manufacture of a medicament for the treatment of Alzheimer's disease wherein apathy is comorbid with Alzheimer's disease.

E24 The embodiment of any of the previous embodiments the Alzheimer's disease, wherein said Alzheimer's disease is at a mild to moderate stage.

E25 The embodiment of any of the previous embodiments the Alzheimer's disease, wherein said Alzheimer's disease is at a moderate to severe stage.

E26. A method for the treatment of Alzheimer's disease wherein apathy is comorbid with Alzheimer's disease, wherein said method comprises administering a therapeutically effective amount of:
(A) a 5-$HT_6$ receptor antagonist selected from the group consisting of one or more of: the compounds idalopirdine, RVT-101, AVN-211, and pharmaceutically acceptable salts of such compounds; and
(B) an acetylcholinesterase inhibitor selected from the group consisting of one or more of: the compounds donepezil, rivastigmine, galantamine, and pharmaceutically acceptable salts of such compounds;
to a patient in need thereof.

Definitions

Throughout the specification, the term "5-$HT_6$ receptor antagonist" as well as any specific 5-$HT_6$ receptor antagonist, such as idalopirdine, AVN-211 or RVT-101, is intended to include, unless otherwise specified, any form of the compound, such as the free base and pharmaceutically acceptable salts. The free base and pharmaceutically acceptable salts include anhydrous forms and solvated forms such as hydrates. The anhydrous forms include amorphous and crystalline forms, and the solvates include crystalline forms. Further, unless otherwise specified, the term "5-$HT_6$ receptor antagonist" includes the human 5-$HT_6$ receptor antagonist (which also may be denoted "h5-$HT_6$ receptor antagonist").

Likewise, the term "acetylcholinesterase inhibitor" (abbreviated "AChEI") as well as any specific acethylcholinesterase inhibitor, such as "donepezil", is intended to include any form of the compound, such as the free base and pharmaceutically acceptable salts etc.

The term "acetylcholinesterase inhibitor" (AChEI) is known to those skilled in art and includes compounds selected from the group consisting of donepezil ((RS)-2-[(1-Benzyl-4-piperidyl)methyl]-5,6-dimethoxy-2,3-dihydroinden-1-one), rivastigmine ((S)-3-[1-(dimethylamino)ethyl]phenyl N-ethyl-N-methylcarbamate), galantamine ((4aS,6R,8aS)-5,6,9,10,11,12-Hexahydro-3-methoxy-11-methyl-4aH-[1]benzofuro[3a,3,2-ef][2]benzazepin-6-ol) and tacrine (1,2,3,4-tetrahydroacridin-9-amine). The FDA approved dosages of the acetylcholinesterase inhibitor are encompassed by the instant invention. For example, the dosages of donepezil are shown to be effective in controlled clinical trials of the treatment of mild to moderate Alzheimer's disease are 5 mg or 10 mg administered orally once per day. A 23 mg orally once daily dose of donepezil is also approved for treating moderate to severe AD.

In the present context, when a 5-$HT_6$ receptor antagonist, such as idalopirdine, AVN-211 or RVT-101, or any other 5-$HT_6$ receptor antagonist, is used in combination with an AChEI, such as donepezil, rivastigmine, tacrine or galantamine, this indicates in one embodiment that said two compounds can be administrated simultaneously for example in a pharmaceutical composition comprising both compounds. In another embodiment, when a 5-$HT_6$ receptor antagonist is used in combination with an AChEI, this indicates that said two compounds are administered separately in suitable individual pharmaceutical compositions. These individual compositions may be administered simultaneously e.g. with regular intervals once daily either morning or evening, or they may be administered independently e.g. one compound with regular intervals once daily in the morning and the other compound with regular intervals once daily in the evening.

In the context of the present invention, the terms comorbid and comorbidity refer to one more than one disorders or diseases (such as apathy) that exist alongside a primary diagnosis (such as Alzheimer's disease) that is the reason a patient gets referred and/or treated.

Apathy is in the context of the present invention defined as a score of 1 or higher, such as a score of 2, or 3, or 4, or 6, or 8, or 12 obtained through application of the NPI instrument. The NPI is a 12-item validated structured interview with a caregiver, designed to assess behavioural disturbances in patients with dementia, and includes ten behavioural areas, including apathy, and two neurovegetative areas. The NPI is further described in Cummings J L et al. The Neuropsychiatric Inventory: comprehensive assessment of psychopathology in dementia. *Neurology* 1994; 44: 2308-14.

In the context of the present invention, the terms "Alzheimer's disease with apathy as comorbidity," "Alzheimer's disease with comorbid apathy," and "Alzheimer's disease wherein apathy is comorbid with Alzheimer's disease" are intended to be synonymous and to refer to an Alzheimer's disease condition in which affected subjects exhibit comorbid apathy.

A "therapeutically effective" dose or amount of 5-HT$_6$ receptor antagonist is an amount sufficient to provide an observable therapeutic benefit compared to baseline clinically observable signs and symptoms of Alzheimer's disease as measured by ADAS-cog (Rosen W G et al. A new scale for Alzheimer's disease. *Am J Psychiatry* 1984; 141: 1356-64), and Alzheimer's disease-related dementia treated in connection with the combination therapy.

The term "daily" means a continuous twenty-four (24) hour period.

The term "dose" is used herein to mean administration of 5-HT$_6$ receptor antagonist or acetylcholinesterase inhibitor in one dosage form to the patient being treated. In some embodiments, the dose is a single oral formulation. In some embodiments, the dose is formulated as a tablet, a capsule, a pill, or a patch administered to the patient.

In the present context, a "unit dosage form" refers to a formulation unit of a pharmaceutical composition e.g. a tablet or a capsule.

The term "effective daily dose" means the total amount of 5-HT$_6$ receptor antagonist or AChEI administered to a patient in need of therapy in a continuous, twenty-four (24) hour period. As a non-limiting example used herein solely to illustrate the meaning of the term, an effective daily dose of 90 mg shall mean and include administering a single dose of 90 mg in a twenty-four-hour period, administering two doses of 45 mg each within a twenty-four-hour period, administering three doses of 30 mg each in a twenty-four-hour period, and so on. When administering 5-HT$_6$ receptor antagonist in such a manner, i.e. more than once in a twenty-four-hour period, such administrations can be spread evenly through the twenty-four-hour period or even be administered simultaneously or nearly so, etc.

The term "dose range" as used herein refers to an upper and a lower limit of an acceptable variation of the amount of agent specified. Typically, a dose of the agent in any amount within the specified range can be administered to patients undergoing treatment.

The term "treat" is used herein to mean to relieve, reduce or alleviate at least one symptom of a disease in a subject. For example, in relation to dementia, the term "treat" may mean to relieve or alleviate cognitive impairment (such as impairment of memory and/or orientation) or impairment of global functioning (overall functioning, including activities of daily living) and/or slow down or reverse the progressive deterioration in global or cognitive impairment.

Pharmaceutically Acceptable Salts

The present invention also comprises salts of the 5-HT$_6$ receptor antagonists, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., *J. Pharm. Sci.* 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

In a particular embodiment of the present invention 5-HT$_6$ receptor antagonist is in the form of a hydrochloric salt of idalopirdine.

Pharmaceutical Compositions

The present invention further provides a pharmaceutical composition comprising a therapeutically effective amount of a 5-HT$_6$ receptor antagonist and a pharmaceutically acceptable carrier or diluent. The present invention also provides a pharmaceutical composition comprising a therapeutically effective amount of one of the 5-HT$_6$ receptor antagonist and a pharmaceutically acceptable carrier or diluent.

The 5-HT$_6$ receptor antagonist may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 21$^{st}$ Edition, Gennaro, Ed., Mack Publishing Co., Easton, Pa., 2005.

The pharmaceutical compositions may be specifically formulated for administration by any suitable route such as oral, rectal, nasal, pulmonary, topical (including buccal and sublingual), transdermal and parenteral (including subcutaneous, intramuscular and intravenous) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

The 5-$HT_6$ receptor antagonists of this invention are generally utilized as the free substance or as a pharmaceutically acceptable salt thereof. One example is an acid addition salt of a 5-$HT_6$ receptor antagonist which has the same utility as of a free base. When a 5-$HT_6$ receptor antagonist contains a free base such salts are prepared in a conventional manner by treating a solution or suspension of a free base of the 5-$HT_6$ receptor antagonist with a pharmaceutically acceptable acid. Representative examples of suitable organic and inorganic acids are described above.

For parenteral administration, solutions of the 5-$HT_6$ receptor antagonist in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The 5-$HT_6$ receptor antagonist may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the 5-$HT_6$ receptor antagonist and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tableted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tableting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

The 5-HT6 receptor antagonist is generally utilized as the free substance or as a pharmaceutically acceptable salt thereof. Examples of suitable organic and inorganic acids are described above.

Dosing Regimen

The dosing regimen for the 5-$HT_6$ antagonist will depend on the actual pharmacokinetic profile of the antagonist, but generally the dosing regimen will comprise a dose range of 5-200 mg/day, dosed once or twice daily. For idalopirdine the preferred dosing regimen will comprise a dose range of 10-90 mg/day, dosed once or twice daily, preferably once daily. The preferred dosing regimen for idalopirdine is a dose range of 30-60 mg/day, dosed once daily.

The dosing regimen for the AChEI will depend on the actual pharmacokinetic profile of the inhibitor, but generally the dosing regimen will comprise a dose range of 5-200 mg/day, dosed once or twice daily. Galantamine is typically dosed from 8 mg/day to 24 mg/day, rivastigmine is typically dosed from 3 mg/day to 12 mg/day, and donepezil is typically dosed from 5 mg/day to 23 mg/day, each dosed once or twice daily.

The 5-$HT_6$ antagonist may be administered simultaneously with an AChEI or the 5-$HT_6$ antagonist and the AChEI may be administered independently of each other.

In the case wherein the 5-$HT_6$ antagonist is administered simultaneously with an AChEI the two compounds may be contained in the same unit dosage form (e.g. a single tablet comprising both the 5-$HT_6$ receptor antagonist and an AChEI) or in separate unit dosage forms (e.g. two tablets comprising the 5-HT$_6$ receptor antagonist and an AChEI respectively).

Unless otherwise specified the dose is calculated on the basis of the free base of the active pharmaceutical ingredient.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The use of the terms "a" and "an" and "the" in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

Experimental

EXAMPLE 1

Binding Affinity of Idalopirdine

Previously conducted in vitro binding studies have reported (Arnt J, et al. Lu AE58054, a 5-HT$_6$ receptor antagonist, reverses cognitive impairment induced by subchronic phencyclidine in a novel object recognition test in rats. *Int J Neuropsychopharmacol* 2010; 13: 1021-1033) that N-(2-(6-fluoro-1H-indol-3-yl)-ethyl)-3-(2,2,3,3-tetrafluoropropoxy)-benzylamine is a potent and selective human 5-HT$_6$ receptor antagonist with the following affinity for human 5-HT$_6$ receptor and other human 5-HT receptor subtypes:

TABLE 1

Inhibition of 5-HT receptors by idalopirdine

| Receptor | K$_i$(nM) |
|---|---|
| h5-HT$_6$ | 0.83 |
| h5-HT$_{1A}$ | 2300 |
| h5-HT$_{1B}$ | >10,000 |
| h5-HT$_{1D}$ | 2600 |
| h5-HT$_{1E}$ | >4600 |

TABLE 1-continued

Inhibition of 5-HT receptors by idalopirdine

| Receptor | K$_i$(nM) |
|---|---|
| h5-HT$_{1F}$ | 2400 |
| h5-HT$_{2A}$ | 83 |
| h5-HT$_{2B}$ | >4100 |
| h5-HT$_{2C}$ | 250 |
| h5-HT$_7$ | >10,000 |

EXAMPLE 2

The LADDER Study

The LADDER study that was conducted to assess the effect on cognitive performance of idalopirdine in donepezil-treated patients with moderate Alzheimer's disease.

The LADDER study is registered with ClinicalTrials.gov, number NCT01019421 and is reported in Wilkinson D, et al. Safety and efficacy of idalopirdine, a 5-HT$_6$ receptor antagonist, in patients with moderate Alzheimer's disease (LADDER): a randomised, double-blind, placebo-controlled phase 2 trial *Lancet Neurol* 2014; 13: 141-49.

278 patients, both male and female, aged 50 years or older, a mini-mental state examination (MMSE) score of 12-19 at screening and baseline, and who had been treated daily with donepezil for 4 months or more and stable on 10 mg per day for 3 months or more before screening, were eligible for inclusion in the study. Patients were randomly assigned (1:1) to double-blind treatment with idalopirdine or placebo.

The cognitive subscale of the 70-point, 11-item Alzheimer's Disease Assessment Scale (ADAS-cog) was rated at baseline and at weeks 4, 12, and 24. The ADAS-Cog scale is described in Rosen W G et al. A new scale for Alzheimer's disease. *Am J Psychiatry* 1984; 141: 1356-64. The change from baseline in the ADAS-cog at week 24 was the primary endpoint and the study showed that improvement in cognitive function was significantly better with idalopirdine than with placebo.

In addition, a number of secondary efficacy endpoints were pre-specified and assessed at week 24. None of the effects of idalopirdine on the pre-specified secondary endpoints were statistically significant at week 24.

EXAMPLE 3

Treatment Effect of Idalopirdine on Cognition in Patients Suffering from Alzheimer's Disease wherein Apathy is Comorbid Subsequent to the analysis of the primary and secondary endpoints of the LADDER study as described in Example 2 above a post-hoc analysis was conducted. The post-hoc analysis focused on patients enrolled in the study with an apathy score of 1 or higher as measured by neuropsychiatric inventory (NPI) secondary efficacy endpoint.

About 44% of the enrolled patients had an apathy score of 1 or higher at baseline:

TABLE 2

Apathy score at baseline for patients enrolled in the LADDER study

| Apathy score (NPI) | Frequency |
|---|---|
| 0 | 156 |
| 1 | 14 |
| 2 | 22 |
| 3 | 18 |
| 4 | 36 |
| 6 | 16 |
| 8 | 11 |
| 12 | 5 |

For the post-hoc analysis apathy was considered present if the apathy score as measured by Neuropsychiatric Inventory (NPI) was 1 or higher.

The statistical analysis predicted a significant interaction at a 5% significance level between apathy score and treatment effect of idalopirdine on cognition as measured by the ADAS-Cog score (a negative score means less decline in cognitive skills and is thus desirable):

TABLE 3

Estimated change in effect on cognition at week 24 per unit increase in NPI apathy item score

| | Estimate | P-value | Lower | Upper |
|---|---|---|---|---|
| Change in effect on cognition at week 24 per unit increase in NPI apathy item score | −0.64 | 0.030 | −1.2 | −0.062 |

The predicted interaction is also reflected in the actual efficacy estimates of the treatment with idalopirdine in the two subgroups (with or without apathy)

TABLE 4

Effect on cognition at week 24 in patients with and without apathy

| | Estimate |
|---|---|
| Effect on cognition at week 24 in patients without apathy | −0.81 |
| Effect on cognition at week 24 in patients with apathy | −3.8 |

EXAMPLE 4

Treatment Effect of Idalopirdine on Activities of Daily Living (ADL) in Patients Suffering from Alzheimer's Disease wherein Apathy is Comorbid The same patient population as in Example 3 was analysed in a post-hoc analysis. For the post-hoc analysis apathy was considered present if the apathy score as measured by Neuropsychiatric Inventory (NPI) was 1 or higher.

The statistical analysis predicted a significant interaction at a 5% significance level between apathy score and treatment effect of idalopirdine on Activities of Daily Living as measured by the ADCS-ADL score (Galasko et al; An inventory to assess activities of daily living for clinical trials in Alzheimer's Disease. Alzheimer Dis Assoc Disord. 1997; 11(Suppl 2):22-32) (a positive score means an improvement):

TABLE 5

Estimated change in effect on ADL at week 24 per unit increase in NPI apathy item score

| | Estimate | P-value | Lower | Upper |
|---|---|---|---|---|
| Change in effect on ADL at week 24 per unit increase in NPI apathy items core | 0.92 | 0.039 | 0.048 | 1.8 |

The predicted interaction is also reflected in the actual efficacy estimates of the treatment with idalopirdine in the two subgroups (with or without apathy)

TABLE 6

Effect on ADL at week 24 in patients with and without apathy

| | Estimate |
|---|---|
| Effect on ADL at week 24 in patients without apathy | 0.39 |
| Effect on ADL at week 24 in patients with apathy | 2.89 |

These observations were novel and unexpected as there is no prior established treatment with enhanced efficacy for patients with Alzheimer's disease and comorbid apathy, neither in terms of improvement in cognition nor ADL.

Assays

5-HT binding affinity was determined as described in Arnt J, et al. Lu AE58054, a 5-$HT_6$ receptor antagonist, reverses cognitive impairment induced by subchronic phencyclidine in a novel object recognition test in rats. *Int J Neuropsychopharmacol* 2010; 13: 1021-1033.

Relevant psychiatric tests (ADAS-cog and apathy evaluated by NPI) have been referenced in the description above and are hereby incorporated in full.

What is claimed is:

1. A method for improving activities of daily living in a subject with Alzheimer's Disease and comorbid apathy, comprising administration of (i) a therapeutically effective amount of a $5HT_6$ receptor antagonist or pharmaceutically acceptable salt thereof, and (ii) an acetylcholinesterase inhibitor or a pharmaceutically acceptable salt thereof to said subject.

2. The method of claim 1, wherein said 5-$HT_6$ receptor antagonist is selected from the group consisting of:
N-(2-(6-fluoro-1H-indol-3-yl)-ethyl)-3-(2,2,3,3-tetrafluoropropoxy)-benzylamine, 3-Benzenesulfonyl-5,7-dimethyl-2-methylsulfanyl-pyrazolo[1,5-a]pyrimidine, and 3-phenylsulfonyl-8-piperazin-1-yl-quinoline.

3. The method of claim 1, wherein said 5-$HT_6$ receptor antagonist is a pharmaceutically acceptable salt of N-(2-(6-fluoro-1H-indol-3-yl)-ethyl)-3-(2,2,3,3-tetrafluoropropoxy)-benzyl amine.

4. The method of claim 3, wherein said 5-$HT_6$ receptor antagonist is the hydrochloride salt of N-(2-(6-fluoro-1H-indol-3-yl)-ethyl)-3-(2,2,3,3-tetrafluoropropoxy)-benzylamine.

5. The method of claim 2, wherein the acetylcholinesterase inhibitor is selected from the group consisting of the compounds: donepezil, rivastigmine and galantamine, or is a pharmaceutically acceptable salt of such compounds.

6. The method of claim 2, wherein the acetylcholinesterase inhibitor is the hydrochloride salt of donepezil.

7. The method of claim 1, wherein the 5-$HT_6$ receptor antagonist is the hydrochloride salt of N-(2-(6-fluoro-1H-indol-3-yl)-ethyl)-3-(2,2,3,3-tetrafluoropropoxy)-benzylamine, and the acetylcholinesterase inhibitor is the hydrochloride salt of donepezil.

8. The method of claim 3, wherein the dosing range of said 5-$HT_6$ receptor antagonist is from 30 mg/day to 60 mg/day.

9. The method of claim 4, wherein the dosing range of said 5-$HT_6$ receptor antagonist is from 30 mg/day to 60 mg/day.

10. The method of claim 5, wherein said 5-$HT_6$ receptor antagonist is N-(2-(6-fluoro-1H-indol-3-yl)-ethyl)-3-(2,2,3,3-tetrafluoropropoxy)-benzyl amine and wherein the dosing range of said 5-$HT_6$ receptor antagonist is from 30 mg/day to 60 mg/day.

11. The method of claim 6, wherein said 5-$HT_6$ receptor antagonist is N-(2-(6-fluoro-1H-indol-3-yl)-ethyl)-3-(2,2,3,3-tetrafluoropropoxy)-benzyl amine and wherein the dosing range of said 5-$HT_6$ receptor antagonist is from 30 mg/day to 60 mg/day.

12. The method of claim 7, wherein the dosing range of said 5-$HT_6$ receptor antagonist is from 30 mg/day to 60 mg/day.

13. The method of claim 1, further comprising treating cognitive impairment in the subject with Alzheimer's Disease and comorbid apathy.

14. The method of claim 1, further comprising identifying the subject with Alzheimer's Disease and comorbid apathy prior to administration.

15. The method of claim 13, further comprising identifying the subject with Alzheimer's Disease and comorbid apathy prior to administration.

* * * * *